United States Patent [19]

Curutchet

[11] 4,192,314

[45] Mar. 11, 1980

[54] SURGICAL INSTRUMENTS

[76] Inventor: Pedro D. Curutchet, Sarmiento 156, Loberia, Provincia de Buenos Aires, Argentina

[21] Appl. No.: 845,768

[22] Filed: Oct. 26, 1977

[30] Foreign Application Priority Data

Oct. 27, 1976 [AR] Argentina ............................... 265253

[51] Int. Cl.² ............................................. A61B 17/28
[52] U.S. Cl. ................. 128/322; 81/428 R; 128/318; 128/325; 128/340
[58] Field of Search ............... 128/321, 322, 325, 340, 128/346, 318; 81/428 R; 30/87, 254; 32/62

[56] References Cited

U.S. PATENT DOCUMENTS

| 3,393,680 | 7/1968 | Curutchet | 128/321 |
| 3,407,816 | 10/1968 | Curutchet | 128/321 X |

FOREIGN PATENT DOCUMENTS 966277  8/1964  United Kingdom ..................... 128/321

*Primary Examiner*—Robert W. Michell
*Assistant Examiner*—Michael H. Thaler
*Attorney, Agent, or Firm*—Ladas, Parry, Von Gehr, Goldsmith & Deschamps

[57] ABSTRACT

A surgical instrument comprises two elongate members which are pivoted together intermediate their ends in crossing relationship, so as to define a major plane extending substantially perpendicular to the axis of pivotal movement of the members and in which the members move during relative pivotal movement thereof. Each member has at one end an operating portion which cooperates with the operating portion of the other member when the two operating portions are brought together by relative pivotal movement of the two members. Each member has at its opposite end an actuating key which can be urged towards the actuating key of the other member for bringing the operating portions into cooperating disposition. Each actuating key comprises a substantially rectangular plate which extends transversely to the major plane of the instrument whereby force can be applied to urge the actuating keys together.

8 Claims, 3 Drawing Figures

SURGICAL INSTRUMENTS

This invention relates to surgical instruments.

Single-bladed instruments such as knives, when properly gripped, project forward, following the longitudinal axis of the hand and may therefore be termed aximanual instruments, as distinguished from a crucimanual ring instrument such as a pair of scissors which, when gripped has its points oriented sideways so that the axis of the instrument extends transversely to the longitudinal axis of the hand. In surgery, where the work is performed in the forward direction, aximanual instruments should be used. However, many surgical instruments in use today, such as scissors, needle holders, hemostatic pincers etc., are crucimanual ring instruments. Use of these crucimanual ring instruments by modern surgeons originated from the scissors used by the barber-surgeons at the end of the 15th century. Scissors cut flatwise and not point-first as required in surgery.

Hemostatic pincers are constructed similarly to a pair of scissors except that the blades are arranged to grip instead of to cut. Adjacent the rings, the pincers have toothed racks which engage each other when the blades are in gripping condition to hold the blades in gripping condition. In order to release the grip, the rings are pressed together and slightly sideways so as to disengage the teeth. The manner of releasing the grip gives rise to the serious problem that the instrument tends to rotate at the moment the toothed racks are disengaged.

In using a pair of scissors, a surgeon might half withdraw his thumb from the ring provided therefor in order to bring the instrument towards an aximanual position. However, this is not possible with hemostatic pincers and thus it may happen that the surgeon works with great difficulty when performing deep hemostasis in the course of an operation because his hand is stiff and flexed to form a right angle with the axis of the instrument.

Conventional hemostatic pincers have toothed racks for retaining the pincers in gripping condition. Normally, each toothed rack has three teeth, but the third tooth is never used except by an inexperienced surgeon who, faced with an emergency, loses his dexterity.

Still another difficulty is operating with a pair of hemostatic pincers is that the instrument is essentially flat, having only length and width, making it necessary to lift it from the table and then successively introduce the thumb and index finger in the rings.

The problems associated with hemostatic pincers are compounded by the fact that as many as eight to twelve pairs of pincers are used for each lancet or pair of scissors that is used.

According to the present invention there is provided a surgical instrument, comprising two elongate members which are pivoted together intermediate their ends in crossing relationship, so as to define a major plane of the instrument extending substantially perpendicular to the axis of pivotal movement of the members and in which the members move during relative pivotal movement thereof, each member having at one end an operating portion which cooperates with the operating portion of the other member when the two operating portions are brought together by relative pivotal movement of the two members, and each member having at its opposite end an actuating key which can be urged towards the actuating key of the other member for bringing the operating portions into cooperating disposition, each actuating key comprising a substantially rectangular plate which extends transversely to the major plane of the instrument whereby force can be applied to urge the actuating keys together.

For a better understanding of the invention and to show how the same may be carried into effect, reference will now be made, by way of example, to the accompanying drawing, in which.

Figure 1:
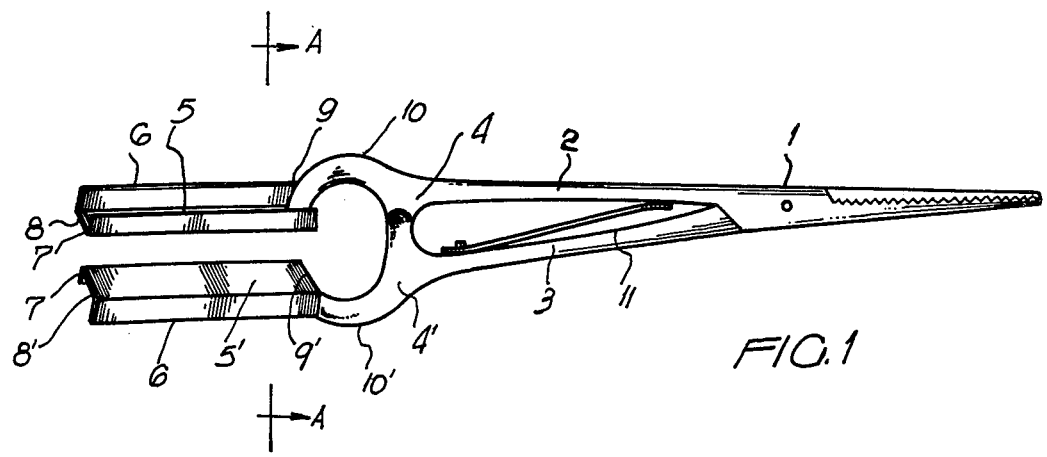
FIG. 1 shows a side view of a hemostatic instrument.
Figure 2:
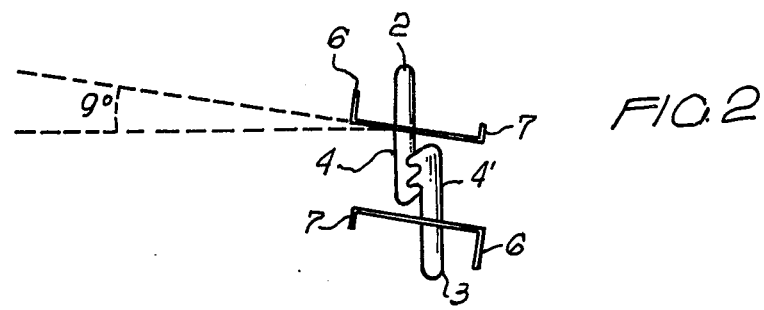
FIG. 2 shows a sectional view taken on the line A—A of FIG. 1.
Figure 3:
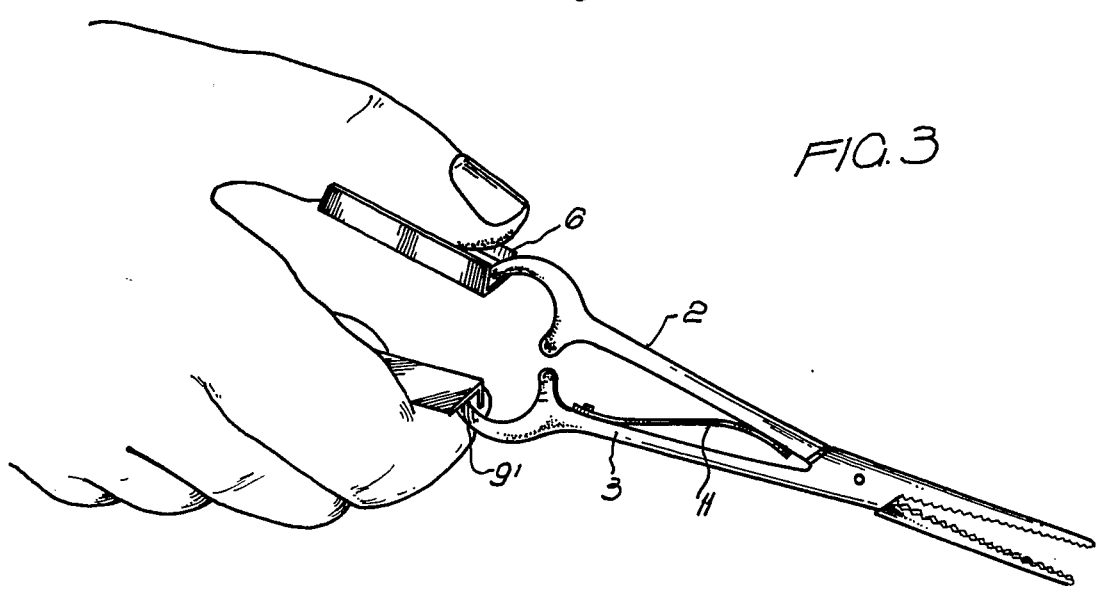
FIG. 3 shows how the instrument may be held in a surgeon's hand.

The illustrated instrument 1 comprises two pivotally-connected members 2 and 3. The forward ends of the members 2 and 3 (the ends to the right of FIG. 1) form opposing jaws. The members 2 and 3 have adjacent their rear ends respective projections formed with opposed interengageable toothed racks 4 and 4'. Each toothed rack has only two teeth, as seen in FIG. 2, and accordingly the racks are short. The members 2 and 3 terminate at their rear ends in respective plate-like keys 5 and 5', instead of in rings.

The keys are inclined at 75° to 85°, preferably about 81°, to the major plane of the instrument, this being a plane which is perpendicular to the axis of pivotal connection of the members 2 and in which the members 2 and 3 move during relative pivotal movement thereof. The inclination of the keys 5, 5' at an angle other than 90° to the major plane is in order to facilitate disengagement of the toothed racks 4, 4' when the keys are pressed together.

The keys 5, 5' give the instrument a three-dimensional quality, so that it projects from the table and when in haste the surgeon can quickly grasp it and bring it to the hemorrhagic point. This is an extremely valuable quality. The third dimension expedites and facilitates handling of the instrument in a single movement.

The two keys 5, 5' are in the form of rectangular plates. Each key is bent at right angles parallel to its long edges to form two wings 6 and 7. Thus, the wings 6 and 7 and the portions of the key therebetween form a recess in which the surgeon's fingers fit. The wings 6 are slightly higher then the wings 7, in order to facilitate application of pressure to the keys in the direction tending to push the members 2 and 3 apart, so as to disengage the toothed racks. The rear edges 8, 8' of the keys extend at right angles to the bend lines at which the wings 6 and 7 are formed, and the front edges 9, 9' of the keys are parallel to the edges 8,8' respectively.

In order to increase the leverage of force applied to the keys 5,5', the members do not terminate immediately to the rear of the toothed racks 4,4' but include extension segments 10,10' extending to the rear of the toothed racks. The presence of these segments not only increases the leverage about the axis of pivotal connection of the members 2 and 3 but also increases the leverage of force applied to the keys 5,5' to push the members 2 and 3 apart for disengaging the toothed racks.

The instrument also includes a spring 11 having one end attached to the member 3 just forward of the toothed rack 4' and extending to the region of the pivotal connection. The spring 11 bears against the member 2 and thus urges the jaws apart.

As in the case of a conventional pair of hemostatic pincers, the members 2 and 3 are divergent to the rear of the pivotal connection. In order to avoid having to spread the hand excessively in use of the instrument, the keys 5,5' do not follow the divergent lines of the members 2 and 3 but are welded to the extension segments 10,10' approximately parallel to each other. In addition, the keys 5,5' are slightly offset from the axes of the members 2 and 3, to the right and left respectively in FIG. 2. This is because the toothed racks 4,4' slightly displace the rear portions of the members 2 and 3 from the major plane of the instrument, to the left and right respectively in FIG. 2, and offsetting of the keys is needed in order to compensate for this effect.

It will be understood that the invention is not limited to the construction shown and described, since it will be apparent to those skilled in the art that modifications may be made without departing from the scope of the invention as defined in the appended claims. For example, the use of plate-like keys instead of rings may be applied to other surgical instruments.

I claim:

1. A surgical instrument, comprising two elongate members which are pivoted together intermediate their ends in crossing relationship, so as to define a major plane of the instrument extending substantially perpendicular to the axis of pivotal movement of the members and in which the members move during relative pivotal movement thereof, each member having at one end an operating portion which cooperates with the operating portion of the other member when the two operating portions are brought together by relative pivotal movement of the two members, and each member having at its opposite end an actuating key which can be urged towards the actuating key of the other member for bringing the operating portions into cooperating disposition, each actuating key comprising a plate which extends transversely to the major plane of the instrument whereby force can be applied to urge the actuating keys together, and each of said plates including a major portion of substantially rectangular form, having two opposite edges which extend substantially parallel to said major plane and two wing portions extending along said opposite edges respectively defining the length of the wing portions and directed away from the other plate defining the width of the wing portions, and wherein that wing portion of one plate which is on one side of the major plane is greater in width than the wing portion of said one plate that is the other side of the major plane, and that wing portion of the other plate which is on said other side of the major plane is greater in width than the wing portion of said other plate that is on said one side of the major plane.

2. An instrument as claimed in claim 1, wherein each elongate member has intermediate its actuating key and the pivotal connection of the members a toothed portion which is engageable with the toothed portion of the other member when the keys are urged together so as to retain the operating portions in cooperating disposition, the toothed portions being disengageable by urging the actuating keys apart in directions transverse to said major plane such that said one plate is urged to said one side of said major plane while said other plate is urged to said other side of said major plane, and each plane is inclined to said major plane at an angle in the range from substantially 75° to substantially 85° whereby a force tending to disengage the toothed portions can be applied to the actuating keys on pressing the actuating keys together.

3. An instrument as claimed in claim 2, wherein the elongate members diverge between the pivotal connection and the toothed portions when the operating portions are in cooperating disposition, yet the plates are so oriented with respect to the elongate members that the plates are substantially parallel when the operating portions are in cooperating disposition.

4. An instrument as claimed in claim 3, wherein each elongate member includes, between and connecting the toothed portion and the actuating key, an arcuate portion curved in said major plane.

5. An instrument as claimed in claim 4, wherein the two arcuate portions are concave towards each other.

6. An instrument as claimed in claim 2, wherein each plate is secured to its elongate member at a position which is nearer the greater width wing portion of the plate than the lesser width wing portion thereof.

7. An instrument as claimed in claim 1, further comprising spring means located between the elongate members, between the pivotal connection and the actuating keys, for urging the actuating keys apart and thereby urging the operating portions out of cooperating disposition.

8. An instrument as claimed in claim 1, wherein each elongate member has intermediate its actuating key and the pivotal connection of the members a toothed portion which is engageable with the toothed portion of the other member when the keys are urged together so as to retain the operating portions in cooperating disposition, the toothed portions being disengageable by urging the actuating keys apart in directions transverse to said major plane such that said one plate is urged to said one side of said major plane while said other plate is urged to said other side of said major plane.

* * * * *